(12) United States Patent
Ginggen et al.

(10) Patent No.: US 7,725,272 B2
(45) Date of Patent: May 25, 2010

(54) METHODS AND DEVICES FOR MONITORING FLUID OF AN IMPLANTABLE INFUSION PUMP

(75) Inventors: Alec Ginggen, Neuchatel (CH); Rocco Crivelli, Bellinzona (CH)

(73) Assignee: Codman Neuro Sciences, SARL, Le Locle (CH)

(*) Notice: Subject to any disclaimer, the term of this patent is extended or adjusted under 35 U.S.C. 154(b) by 837 days.

(21) Appl. No.: 11/278,048

(22) Filed: Mar. 30, 2006

(65) Prior Publication Data

US 2007/0239381 A1    Oct. 11, 2007

(51) Int. Cl.
G06F 19/00    (2006.01)

(52) U.S. Cl. .............. 702/50; 604/288.01; 604/131; 604/132; 604/66; 219/497; 219/494; 392/456; 702/85; 702/100

(58) Field of Classification Search .............. 702/50, 702/85, 100; 604/50, 505, 67, 891.1, 131, 604/132, 65, 24, 134, 234, 236, 288.01, 64, 604/89.1, 500, 66; 219/497, 494; 392/456

See application file for complete search history.

(56) References Cited

U.S. PATENT DOCUMENTS

| 4,013,074 | A |   | 3/1977  | Siposs          |         |
|-----------|---|---|---------|-----------------|---------|
| 4,525,165 | A | * | 6/1985  | Fischell ...... | 604/131 |
| 4,557,722 | A |   | 12/1985 | Harris          |         |
| 4,573,994 | A |   | 3/1986  | Fischell et al. |         |
| 4,760,837 | A |   | 8/1988  | Petit           |         |
| 4,781,685 | A |   | 11/1988 | Lehmann et al.  |         |
| 4,804,054 | A |   | 2/1989  | Howson et al.   |         |
| 4,832,054 | A |   | 5/1989  | Bark            |         |
| 5,006,115 | A |   | 4/1991  | McDonald        |         |
| 5,009,644 | A |   | 4/1991  | McDonald        |         |
| 5,171,228 | A |   | 12/1992 | McDonald        |         |
| 5,527,307 | A |   | 6/1996  | Srisathapat et al. |     |
| 5,637,088 | A |   | 6/1997  | Wenner et al.   |         |
| 5,836,915 | A |   | 11/1998 | Steinbach et al. |        |

(Continued)

FOREIGN PATENT DOCUMENTS

EP    0 678 302    10/1995

(Continued)

OTHER PUBLICATIONS

European Search Report, from corresponding EP Appl. No. 07251359.1, issued Aug. 6, 2007.

*Primary Examiner*—Carol S Tsai
(74) *Attorney, Agent, or Firm*—Nutter McClennen & Fish LLP

(57) ABSTRACT

Methods and devices are described for monitoring reservoir fluid in an implantable infusion pump. Such methods and devices can be used when the infusion pump has a temperature-dependent component. For example, a method of monitoring reservoir fluid can include obtaining measurements from the reservoir that include corresponding data related to the amount of fluid and temperature in the reservoir. A pair of measurements can be used to monitor the fluid level, or flow rate out of, the reservoir when the corresponding temperatures of the measurements are within a temperature tolerance value. In such an instance, a measured amount difference can be calculated based on the fluid amounts corresponding to the pair of measurements. Other variations of fluid monitoring methods, and implantable infusion pump systems that can perform fluid monitoring, are also described.

29 Claims, 5 Drawing Sheets

U.S. PATENT DOCUMENTS

| | | | |
|---|---|---|---|
| 6,049,727 A * | 4/2000 | Crothall | 600/310 |
| 6,259,074 B1 * | 7/2001 | Brunner et al. | 219/497 |
| 6,280,408 B1 * | 8/2001 | Sipin | 604/65 |
| 6,577,899 B2 | 6/2003 | Lebel et al. | |
| 6,740,075 B2 | 5/2004 | Lebel et al. | |
| 6,755,814 B2 | 6/2004 | Wieland et al. | |
| 6,910,377 B1 * | 6/2005 | Richter et al. | 73/290 R |
| 7,291,126 B2 * | 11/2007 | Shekalim | 604/67 |
| 7,374,556 B2 * | 5/2008 | Mallett | 604/132 |
| 2002/0042596 A1 * | 4/2002 | Hartlaub et al. | 604/288.01 |
| 2003/0216683 A1 * | 11/2003 | Shekalim | 604/67 |
| 2004/0133166 A1 | 7/2004 | Moberg et al. | |
| 2006/0150748 A1 * | 7/2006 | Mallett | 73/861.42 |
| 2007/0088267 A1 * | 4/2007 | Shekalim | 604/134 |

FOREIGN PATENT DOCUMENTS

| | | |
|---|---|---|
| WO | WO 00/04944 | 2/2000 |
| WO | WO 04024217 | 3/2004 |

* cited by examiner

METHODS AND DEVICES FOR MONITORING FLUID OF AN IMPLANTABLE INFUSION PUMP

FIELD OF THE INVENTION

The present invention is directed broadly toward devices and methods for monitoring the amount of fluid in a reservoir, and more particularly to monitoring fluid flow from a reservoir of an implantable infusion pump.

BACKGROUND OF THE INVENTION

Various implantable medical devices, often referred to as implantable infusion pumps, are used for dispensing controlled volumes of a drug within a patient's body. Such devices can provide a convenient vehicle for delivering the drug over an extended period of months to years. Such drugs can treat a number of indications including cancer, chronic pain, anti-coagulation, and spasticity.

For infusion pumps that utilize an internal reservoir to hold a supply of drug to be delivered to a patient, periodic refilling of the drug reservoir may be necessary to replenish a depleted drug supply. For example, a syringe needle can be used to inject an additional volume of drug through a septum-covered port connected to the reservoir. Accordingly, timely information regarding the quantity of drug in the reservoir can be a useful feature. Control units associated with regulated operation of an infusion pump can provide data regarding the amount of drug in a reservoir based on the programmed, and expected, operation of the pump by the control unit. Such indirect information, however, can be misleading due to a number potential operating errors (e.g., obstructions or leakages in the drug delivery system).

Though sensors can also be used to determine the quantity of drug remaining in a drug reservoir, sensing devices suitable for use with an implantable infusion pump are still subject to operational constraints that limit their accuracy. For example, measurements from some sensors have a temperature-dependent component that affects the absolute reading provided by the sensor—typically, such sensors are only accurate where the temperature is controlled to within about ±0.1° C. A normal patient's temperature can vary on the order of ±0.4° C., and a patient who is ill can have their temperature vary generally from about 36° C. to about 42° C.—too much for conventional sensors to be accurate. Thus, raw data from such sensors may provide misleading information regarding the quantity of drug remaining in an implantable infusion pump reservoir when the temperature of a patient fluctuates.

Accordingly, a need exists for devices and methods of accurately determining the amount of fluid in a reservoir and/or the fluid flow from a reservoir to help maintain proper operation of an implantable infusion pump.

SUMMARY OF THE INVENTION

One exemplary embodiment is directed to a method of monitoring fluid in a reservoir of an implantable infusion pump. A series of reservoir measurements are obtained, with each measurement including corresponding data related to a fluid amount and a temperature. A first and second measurement can be selected from the reservoir measurements such that a temperature difference, based at least in part on temperatures corresponding with the selected measurements, is less than a temperature tolerance value. Subsequently, a measured amount difference can be calculated based at least in part on fluid amounts corresponding with the selected measurements. The method can be continued by obtaining at least one additional reservoir measurement; selecting two measurements, at least one from the additional measurement(s), such that their temperature difference is less than the temperature tolerance value; and calculating a new measured amount difference based on the selected measurements. These steps can be repeated to continually monitor fluid during the pump operation.

For the exemplary embodiment described above, the reservoir measurements can be obtained as a first series of measurements, and as a second series of measurements collected after the first series. In such an instance, the first measurement can be selected from the first series and second measurement from the second series. In order to identify the first and second measurements, a first candidate measurement can be selected from the first series, and a second candidate measurement selected from the second series. If the temperature difference between the candidate measurements is greater than the temperature tolerance value, either the first or second candidate measurement is replaced. Replacement of a candidate measurement can be based at least upon a measurement time corresponding to at least one of the candidate measurements. The candidate measurements can continue to be replaced until two candidate measurements have a corresponding temperature difference that is less than the temperature tolerance value.

Another exemplary embodiment is directed to monitoring fluid flow from a reservoir of an implantable infusion pump. A series of reservoir measurements are obtained, each measurement including corresponding data related to a fluid amount, a temperature, and a time. In one instance, the fluid amount data can be determined by sending a signal between the pump's control electronics and a sensor. In another instance, the fluid amount data can be identified using a temperature-dependent level sensor, such as coil that produces a variable inductance. A first and second measurement can be selected from the reservoir measurements such that a temperature difference corresponding with the selected measurements is less than a temperature tolerance value. A measured amount difference and a time difference can then be calculated based at least in part on fluid amounts and times corresponding with the selected measurements. The measured amount difference can then be compared with a controlled amount difference, the latter based at least in part on the time difference and the operation of the implantable infusion pump to deliver fluid from the reservoir. The controlled amount difference can also be based on the implantable pump's control electronics. For example, the controlled amount difference can be based on signals sent between the control electronics and a valve used to control flow from the reservoir. The comparison of measured amount difference and controlled amount difference can be performed by comparing a measured flow rate that depends upon the measured amount difference and a controlled flow rate that depends upon the controlled amount difference.

For the above embodiment, comparing the measured amount difference and the controlled amount difference can be used to detect a leakage or blockage in the infusion pump. For example, a leakage can be determined when the measured amount difference exceeds the controlled amount difference by more than a leakage tolerance amount. In another example, a blockage can be determined when the controlled amount difference exceeds the measured amount difference by more than a blockage tolerance amount. Either tolerance amount can depend at least in part on the accuracy of a level sensor used to identify the amount of fluid in the pump reservoir.

Another embodiment is directed to a control system for an implantable infusion pump. Such a control system can be embedded within a portion of the implantable pump. The control system can include a measurement history module for storing reservoir measurements. Each reservoir measurement can include corresponding data related to a temperature, a measured fluid amount, and a time associated with the reservoir measurement. The system can also include one or more processors, electrically coupled to the measurement history module, configured to select two measurements from the measurement history module such that the temperature difference of the selected measurements is less than a temperature tolerance value. A measurement amount difference can be calculated by the processor based in part on the measured fluid amounts corresponding with the selected measurements. A temperature-dependent level sensor (e.g., an inductance-varying coil) can communicate with the measurement history module to determine the fluid amounts in the reservoir. The control system can also include an operating history module that can store operating history data used to regulate flow from a reservoir of the infusion pump. For example, the operating history module can be a valve history module used to store valve operating history data. Such valve operating history data can include a total amount of time that the valve is disposed in at least one of an open position and a closed position over a selected period of time. A valve history module can be electrically coupled to the processor(s), which can be further configured calculate a time difference based at least in part on times corresponding with the selected measurements. The processor(s) can also calculate a controlled amount difference based at least in part on the operating history of the valve and time difference, and can compare the measured amount difference with the controlled amount difference. The comparison can be used to trigger a leakage signal when the measure amount difference exceeds the controlled amount difference by more than a leakage tolerance amount, or can be used to trigger a blockage signal when the controlled amount difference exceeds the measured amount difference by more than a blockage tolerance amount. The processor(s) can also perform the comparison by comparing a measured flow rate and a controlled flow rate, the flow rates being dependent at least in part on the respective amount differences.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
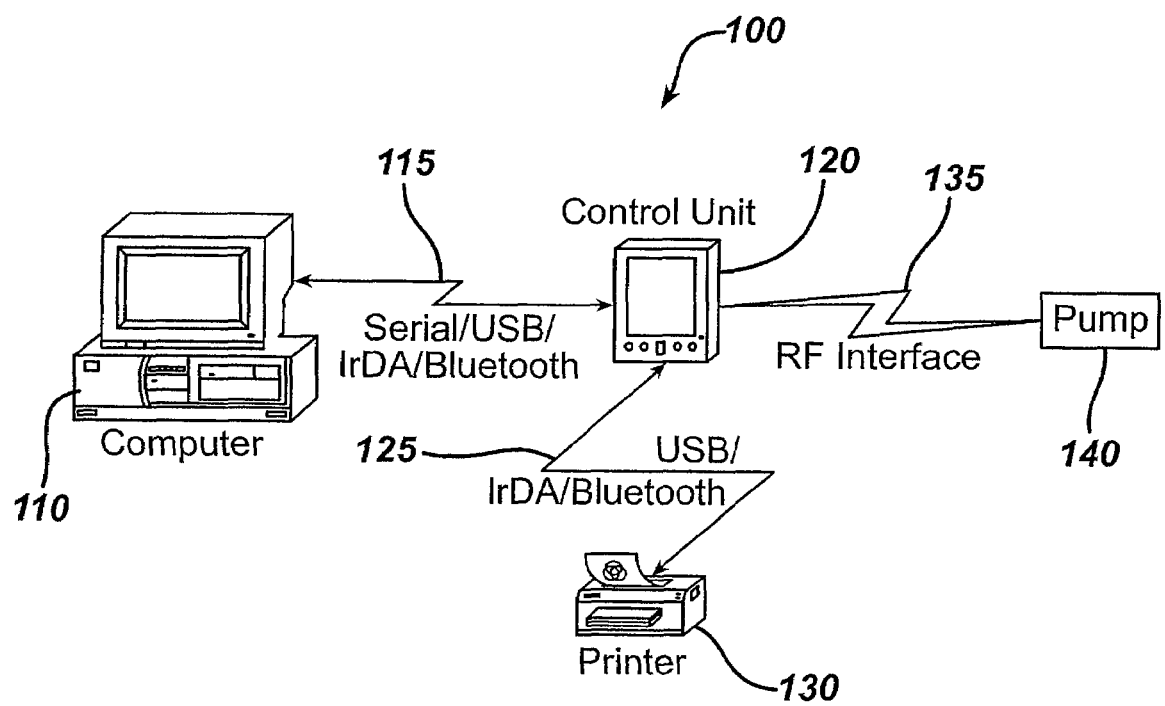
FIG. 1 depicts a schematic diagram of the elements of an exemplary implantable infusion pump system.

Certain exemplary embodiments will now be described to provide an overall understanding of the principles, structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with features of other embodiments. Such modifications and variations are intended to be included within the scope of the present invention.

Some embodiments of the invention are drawn to methods and devices for controlling and/or monitoring the fluid within, and/or the fluid flow out of, an implantable infusion pump. For example, one exemplary embodiment is directed to a method of monitoring fluid in a reservoir of an implantable infusion pump. In general, measurements are obtained from the reservoir of a pump. Corresponding data related to the amount of fluid in the reservoir and a temperature of fluid in the reservoir can be included with each measurement. A first measurement and second measurement can then be selected from the measurements based at least in part on the criteria that the temperatures corresponding to the first and second measurements do not differ by more than a temperature tolerance value. After selection, a fluid amount difference between the two measurements can be calculated based at least in part on the corresponding fluid amounts of each measurement. Methods, such as the one previously described, and devices in accord with the present application can increase the utility of implantable infusion pumps by accounting for temperature fluctuations that affect the functioning of particular components (e.g., sensors, or other control components) of the pumps.

The term "measurement" as utilized herein refers to one or more quantities related to some determination of extent in one or more delineated parameters. For example, a measurement can include one or more datum related to any one of an amount of fluid, temperature, and time associated with measuring fluid in a reservoir of an infusion pump at a particular moment. Accordingly, a "measurement" is not necessarily in the form of the extent of a particular delineated parameter. For example, a measurement of fluid amount can be represented in terms of volume units (e.g., milliliters, cubic centimeters, ounces) or a level height (e.g., centimeters, inches, etc.), or some other extensive variable. Measurements, however, can also be presented in the form of some type of intensive variable that is dimensionless. For example, the level height in a reservoir can be a normalized level height, i.e., the actual level height divided by some reference level height such as the maximum level height when the reservoir is full of fluid. Furthermore, measurements can be represented by any numeric value that can be converted to the desired delineated parameter. For example, frequency can be correlated with an amount of fluid in a reservoir when an inductive coil is used to determine the reservoir fluid level. As such, those skilled in the art will appreciate that a "measurement" can be represented in various manners that can be utilized within the scope of embodiments of the present application.

Implantable Infusion Pumps and Pump Systems

One example of an infusion pump system 100 that can utilize embodiments of the present application is shown in FIG. 1. The infusion pump 140 can be a programmable pump unit that communicates with an external control unit 120. Radiofrequency (RF) telemetry signals 135 can be utilized to provide wireless communication between the control unit 120 and the pump 140. The control unit 120 can also communicate with a computer 110 or a print media unit 130 to download data regarding operation of the pump 140, which can be stored in the control unit 120 or pump 140. Signals 115, 125 between the control unit 140 and the computer 120 and/or the print media unit 130 can be communicated through a wireless protocol (e.g., IrDA, Bluetooth) or a hardwire connection protocol (e.g., serial, USB).

Figure 2:
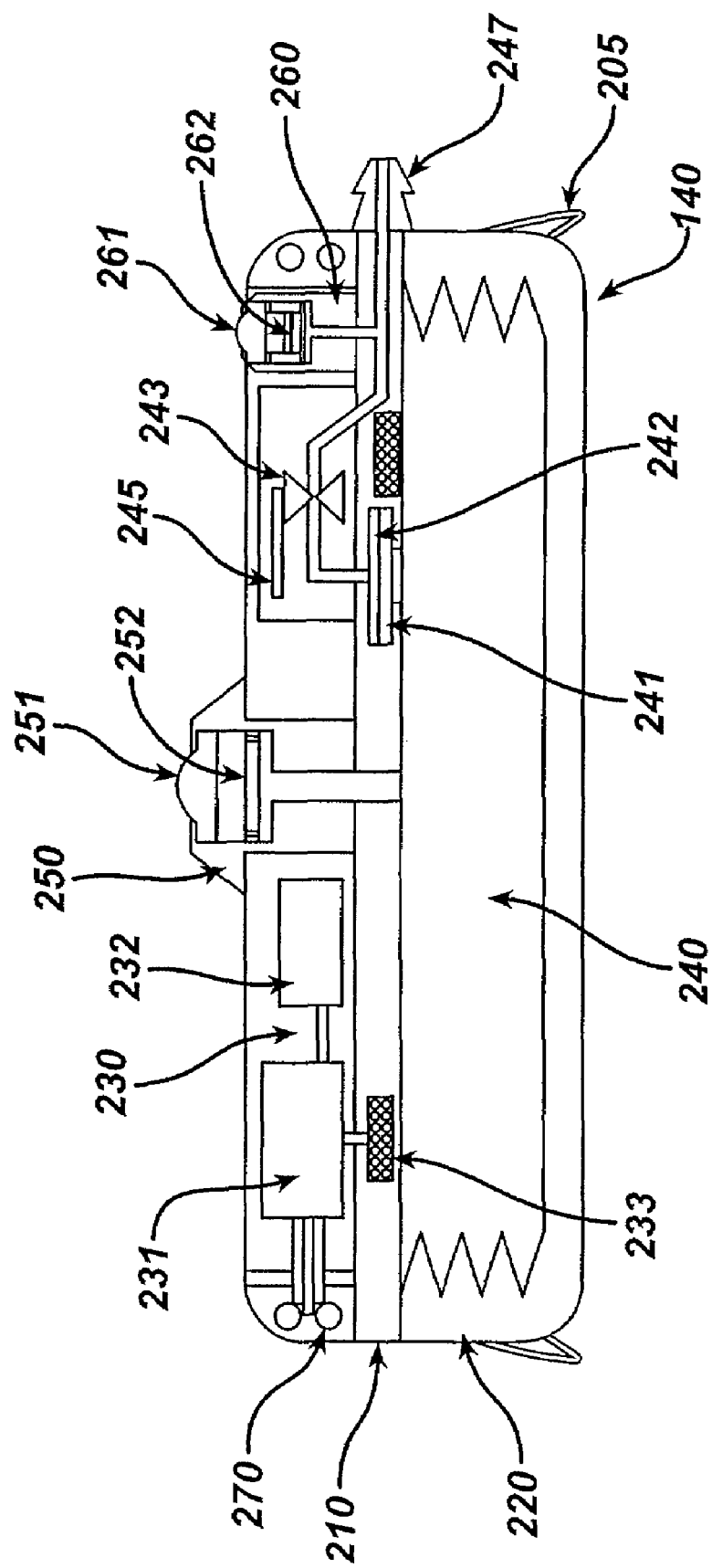
FIG. 2 presents a cross-sectional side-view schematic of an exemplary implantable infusion pump.

An exemplary implantable infusion pump that can be used with the system 100 is schematically depicted in FIG. 2. The infusion pump 140, typically constructed of metal such as titanium, can be configured to be implanted within a patient. Suture loops 205 can help secure the position of the pump 140 and prevent undesirable displacement. The pump 140 can have two separate chambers 220, 240 mounted on the lower side of the pump base plate 210. An outer chamber 220 can contain a pressurized, chemically inert, propellant fluid to exert a substantially constant force onto a titanium bellows enclosure of an inner chamber 240. The inner chamber 240 serves as a reservoir for holding a fluid (e.g., a medicament such as morphine or insulin). The reservoir 240 typically has a volume from about 10 to about 100 mLs (e.g., 20 mLs or 40 mLs). Upon depletion, the reservoir 240 can be refilled with fluid through refill port 250. By inserting a syringe needle through the refill septum 251 up to a plastic needle stop 252, which aids in preventing a needle from penetrating too deeply, the syringe can deliver a new charge of fluid to the reservoir 240. The reservoir 240 can be in fluid communication with a filter 241, a flow restrictor 242, and a valve 243, which affects the fluid flow rate out of the reservoir 240. Valve actuator 245 can be used to open and close valve 243. Fluid leaves the pump 140 through outlet port 247, which can be coupled to a catheter (not shown) to direct fluid to a desired application site. A bolus port can be included to provide a vehicle for bolus injections. The particular bolus port 260 shown in FIG. 2 includes a septum 261 and needle stop 262 to allow needle injection of a bolus. A third chamber 230 can be located on the upper side of the base plate 210 to contain control electronics 231 and a battery 232. The battery 232 (e.g., a lithium ion battery) can be recharged by electrical coupling with a power source unit. A sensor 233, electrically coupled to the control electronics 231, can be configured to detect the amount of fluid in the reservoir 240. The pump 140 can be configured to communicate with a control unit by sending signals via an antenna 270.

In use, the substantially constant force of the propellant fluid in the outer chamber 220 compresses the bellows to force fluid out of the reservoir 240 across the filter 241 through a flow restrictor 242 into the valve module 243. The elements can be configured to force fluid out of the reservoir 240 at a constant rate, which is determined in part by the characteristics of the flow restrictor 242 (e.g., a Pyrex covered silicone chip having a triangular shaped channel) when the valve is in an open position. In one embodiment, the flow rate out of the pump 140 can be controlled by a valve operating in a dual mode that either prevents fluid from flowing through the valve or allows fluid to flow through the valve at a constant rate. Thus, the total amount of time that the valve is open over a given period, determines the amount of fluid leaving the pump 140. For example, the pump components can be configured to deliver between about 0 mLs/day to about 4 mLs/day of fluid, with the valve configured to open over a minimum interval to allow 0.05 mLs of fluid to flow from the reservoir. The total amount of fluid delivered from the pump depends upon the total length of time that the valve is opened, or conversely the amount of time the valve is closed, during an operating day.

A sensor can be used to determine the amount of fluid in the reservoir during pump operation. Those skilled in the art will appreciate that a variety of sensors can be employed to determine the amount of fluid in a reservoir, including sensors having a temperature-dependent component. In one instance, the sensor 233 depicted in FIG. 2 can be a fluid level sensor that provides a signal indicative of the level of fluid in the reservoir 240 of the pump 140. For example, the fluid level sensor can be configured to produce a level signal, which depends upon the distance between an inductive coil 233 and the base of the bellows that rises as fluid is expelled from the reservoir 240. The inductance of the coil 233, which depends upon the amount of fluid and the fluid temperature in the reservoir 240, can be converted to a frequency signal that is subsequently converted to some measure of fluid level in the reservoir 240. Since the coil inductance is also a function of temperature, the sensor can be temperature calibrated to insure an acceptable correlation between frequency and a corresponding fluid level in the reservoir. For example, the sensor can be calibrated at about 37° C. to provide a correlation between frequency and fluid level near normal body temperature. Such a calibration can result in a fluid level accuracy corresponding to a reservoir volume accuracy of about ±2 mLs when the pump operates at a temperature of about 37° C.±0.5° C. In another example, when a 40 mLs volume reservoir is utilized, the calibration can result in a fluid level accuracy corresponding to ±5 mLs when the reservoir has a total volume between about 20 mLs and about 40 mLs, and a fluid level accuracy corresponding to ±2 mLs when the reservoir has a total volume between about 0 mLs and about 20 mLs.

As previously mentioned, the system and pump depicted in FIGS. 1 and 2 are examples of potential implantable infusion pump systems and pumps that can be utilized within the scope of the present application. Those skilled in the art will readily appreciate that numerous other systems and pumps can be utilized with the devices and methods described herein. For example, the system shown in FIG. 1 need not utilize a separate control unit, or the various elements need not utilize the explicitly mentioned communications protocols described earlier. In another example, an infusion pump can be configured with different components and operational features than the exemplary pump of FIG. 2, such as having a separate battery pack that is wired to the pump unit. As well, other types of sensors can be utilized to provide a measure of the amount of fluid in a pump reservoir at a given operational time. Indeed, other systems and pumps can be used with various embodiments described herein so long as they have the components and functionality to practice the specific embodiment.

Control Systems and Electronics for an Implantable Infusion Pump

Figure 3:
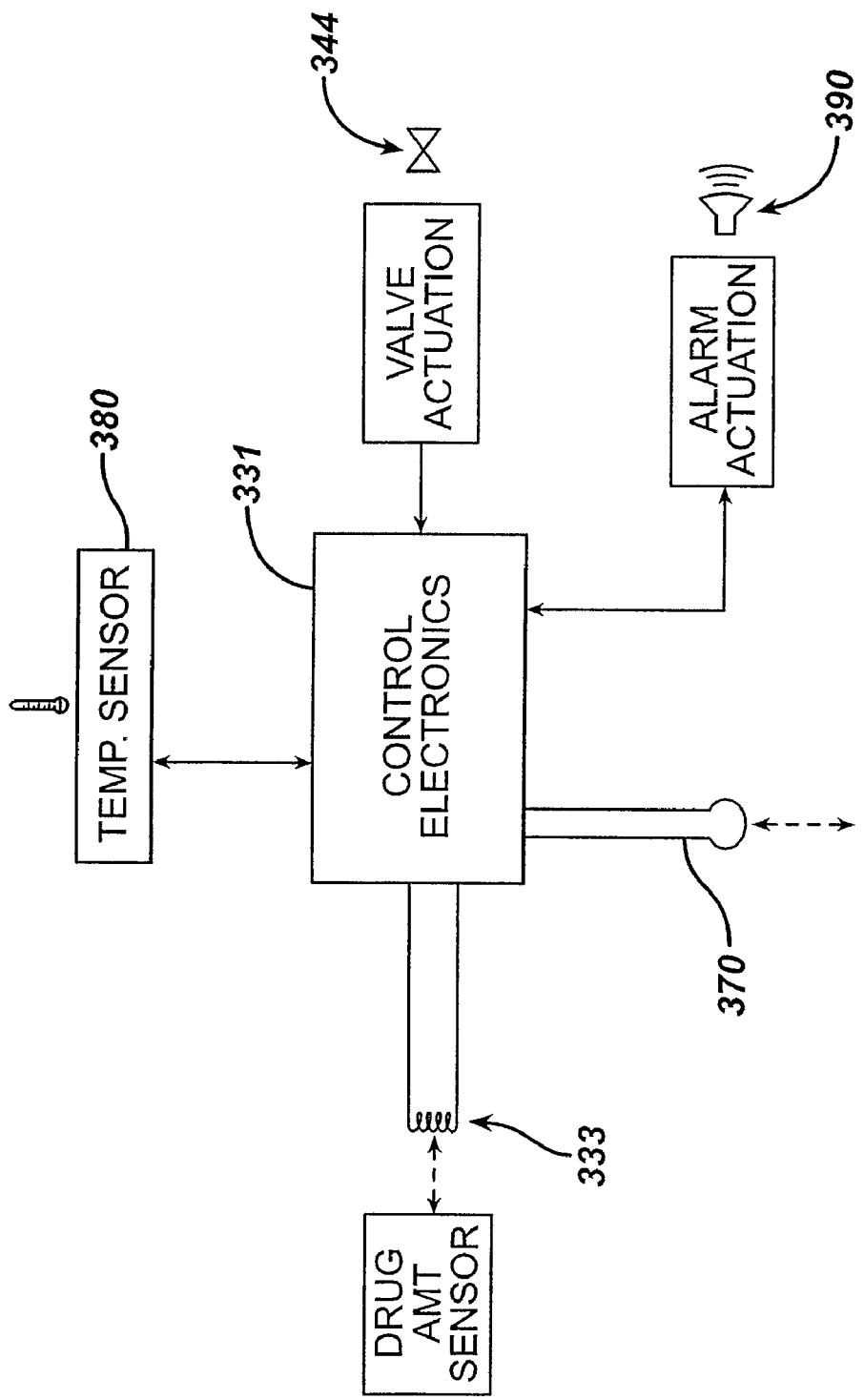
FIG. 3 depicts a schematic diagram of the connections between various infusion pump elements and the pump's control electronics.

The control electronics of an implantable infusion pump can act to generally facilitate the operation of the various components of the pump. The diagram of FIG. 3 depicts exemplary connections that can be generally utilized between the control electronics and some components of the implantable infusion pump. Control electronics 331 can be coupled to a fluid amount sensor (e.g., a level sensor with an inductive coil 333) to provide access to the amount of fluid remaining in a infusion pump reservoir. When an inductive coil is utilized in a sensor, or the sensor/pump utilizes some other temperature-dependent component, the control electronics 331 can also be connected to a temperature sensor 380 (e.g., a thermocouple) such that the electronics 331 can also receive temperature data. The electronics 331 can also be coupled to actuators that mechanically operate pump components such as a flow valve 344 and an alarm system 390. Alarms, in the form or audio or visual indicators (e.g., illuminated display, lamp indicator, sound signal, or any combination thereof) can provide useful indicators of sub-optimal or non-operative functioning of various pump components. Alarm signaling can be provided as an indication of various pump operations such as low battery power, low reservoir fluid volume, a pump flow rate that deviates from an expected value (e.g., too high or too low), or an environmental temperature that is too low, or too high, to provide expected pump operations. An alarm can also include shutting-off one or more particular pump operations that are malfunctioning, or a shutting-off the entire pump. A connection between the control electronics 331 and an antenna 370 can also be included to allow the pump to communicate with remote modules, such as a control unit as depicted in FIG. 2. Control electronics can be configured in a variety of hardware schemes to achieve control objectives. For example, in one exemplary control electronics scheme, the electronics can be implemented using three microcontrollers: a main microcontroller for performing housekeeping operations and RF communications with the external control unit; a prescription rate microcontroller for implementing real-time clock functioning, drug flow rate control, and power supply control; and a frequency shift keying (FSK) microcontroller for generating FSK frequencies for universal asynchronous receiver-transmitter data.

Figure 4:
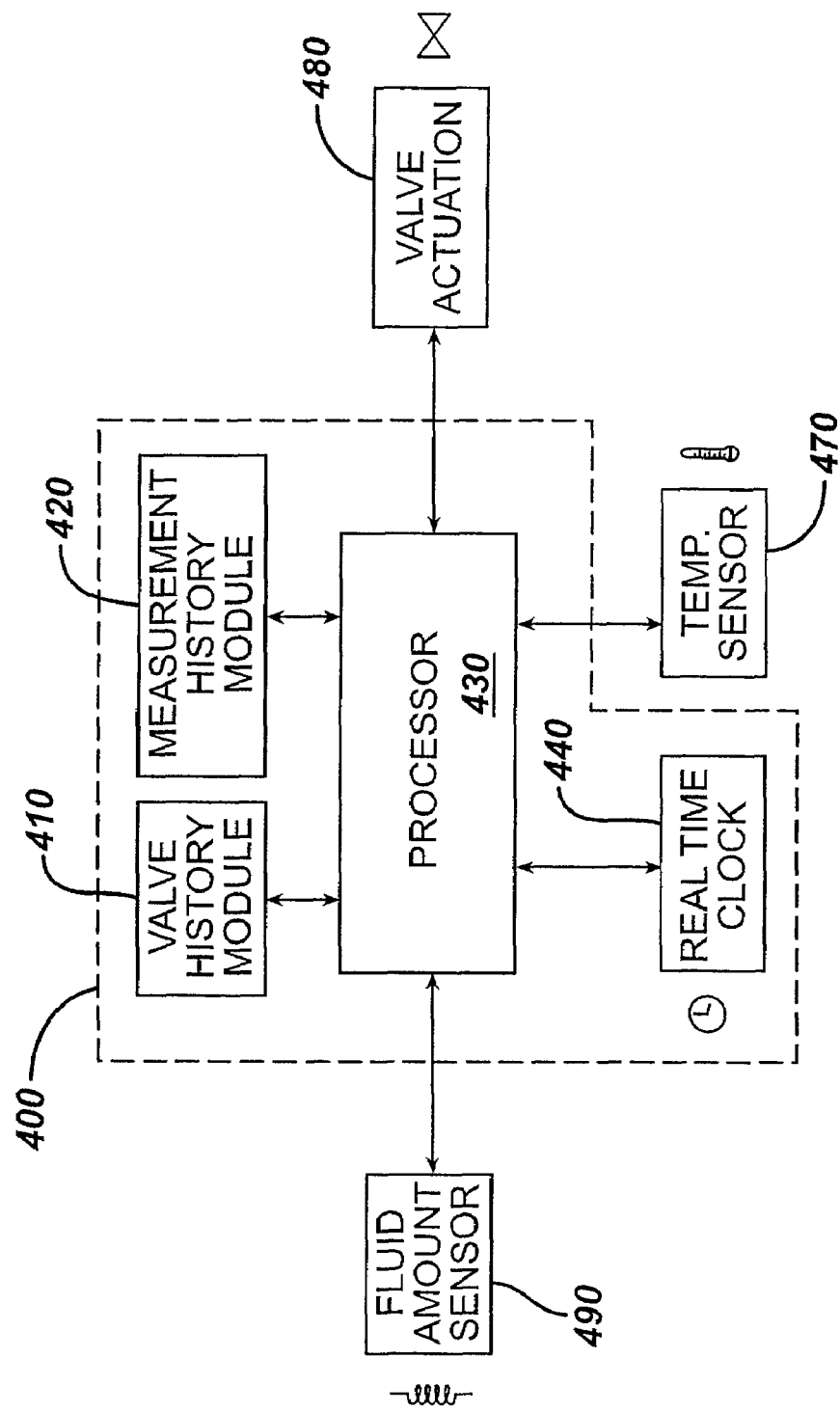
FIG. 4 presents a block diagram of a control system for monitoring the fluid of an implantable infusion pump.

Some embodiments of the present application utilize the control electronics of an implantable infusion pump as a portion, or an entirety, of a system for monitoring fluid within, and/or controlling fluid flow from, a fluid reservoir. The schematic diagram of FIG. 4 presents one exemplary embodiment of a control system 400 for manipulating fluid associated data. It should be recognized that the control system 400 can be a portion of a larger control system for globally controlling the implantable infusion pump, as described earlier. The control system 400 includes a measurement history module 420 electrically coupled to at least one processor 430. The measurement history module 420, which can be used to store a plurality of measurements from the reservoir, can be embodied as a portion of, or an entirety of, a data storage device such as random access memory of a microprocessor. Each of the measurements can include corresponding data related to temperature, a measured fluid amount, and/or a time associated with the measurement. As shown in FIG. 4, the processor 430 can be coupled to a temperature sensor 470 and a fluid amount sensor 490 (e.g., a temperature dependent sensor such as a inductance varying coil) to provide measurement data to the measurement history module 420 of the control system 400. For example, when the fluid amount sensor 490 is embodied as an inductive coil, the coil can transmit a frequency signal to the processor 430 indicative of a fluid level in the reservoir. Subsequently, a look-up table, based upon the temperature calibration of the coil and stored in a memory component (not shown) of the processor 430, can be used to convert the received frequency signals into a corresponding level value. In FIG. 4, the control system 400 can include a real time clock 440 (e.g., a clock as a portion of a processor) to provide time data for the measurement history module 420.

The processor 430 of the exemplary embodiment in FIG. 4 can generally be embodied in a variety of hardware configurations such as a microprocessor, some type of data comparator, some type of data calculator, a portion of an actual microprocessor (e.g., a microprocessor minus its memory components), or a combination of such components. In one embodiment, the processor 430 is configured to select two measurements from the measurement history module 420 based at least in part on the criteria that the temperature difference between the two measurements is less than a temperature tolerance value. Such a criteria can be used to insure that when one examines two temperature-dependent measurements, the corresponding data can be accurately compared. Accordingly, the temperature tolerance value can be selected on any one, or a combination of, criteria that is typically related to the operation of one or more components of the pump. In an exemplary instance, the temperature tolerance value can be based upon a temperature calibration of an inductive coil of a level sensor, which is known to be accurate within a particular temperature range. In particular, if two measurements are within a particular temperature range of one another (i.e., their difference is less than a temperature tolerance value), the range depending in part upon the temperature at which the inductive coil is calibrated, the corresponding level measurements can be compared within a known accuracy range. In a particular example, two measurements separated by a time of at least 18 hours can have a corresponding temperature difference that is less than about ±0.125° C. such that the level measurements can be compared with an acceptable degree of accuracy. In this example, the calibration of the coil is at about 37° C., and accordingly, each of the measurement temperatures should not deviate unacceptably from the calibration temperature. Thus, the processor 430 can also be configured to compare whether each selected measurement has a temperature within a temperature range of the calibration temperature, such as ±1° C.

The processor 430 can also calculate a measured amount difference that depends at least upon the measured fluid amounts corresponding to the two selected measurements as discussed above. For example, the measurement amount difference can be the difference between two level measurements of a reservoir level sensor. Such a difference can be converted into a volume of fluid that can be correlated with the amount of fluid within a reservoir and/or the fluid flow rate from the reservoir (or through the valve or pump generally) over a period of time.

The exemplary embodiment of FIG. 4 can also include an operating history module, e.g., a valve history module 410, coupled to the processor 430, for storing operating history data of a valve that can be used to control flow from the pump reservoir. In such an instance, after a processor selects two measurements, as described above, the processor can calculate a time difference between the measurements based at least in part on a clock time corresponding with each of the measurements. For example, the time difference can correspond with the total elapsed time between the two measurements. The processor can subsequently calculate a controlled amount difference in the reservoir based upon the time difference and some controlled pump function such as the operating history of the valve. This controlled amount difference can be compared with a measured amount difference, as described earlier. Such a comparison can be used as an indicator of pump operation.

Operating history data can include some measure of valve position over a period of time. For example, the data can be embodied as an ensemble of time versus valve opening settings over a particular time period. For some implantable infusion pumps, each valve opening setting can be associated with a particular controlled flow rate through the valve under typical operating conditions (e.g., no leakages or blockages in the pump mechanism or reservoir). Thus, a calculation of the flow through the valve when the valve is in a particular setting can be obtained by the product of the total time that the valve is in the particular setting and the associated controlled flow rate. Adding the contributions from each setting provides a total flow rate through the valve. This, in turn, can be related to the amount of fluid released from the reservoir of the pump, providing a measure of the controlled amount difference of fluid in the reservoir based upon the valve operation. In one instance, as previously described, a valve is operated to either be in a closed position or a predetermined open position. Accordingly, operating history data can be embodied as the amount of time that a valve is in the open position (or closed position) over a given time period. Those skilled in the art will appreciate that other ways of integrating a valve's position, optionally with the other characteristics of a pump's operation, over time to calculate the flow from an infusion pump.

Alternatives to utilizing a valve to control flow from a reservoir can also be implemented in a control electronics scheme. Such alternatives can be implemented with pumps other than an implantable infusion pump as well. For example, if a peristaltic pump is used to deliver liquid drug from a reservoir, the control electronics of the system in FIG. 4 can be modified to control the peristaltic pump. In particular, the valve history module can be replaced with a operating history module that includes some measure of how the peristaltic pump is operating over a given period of time. If the peristaltic pump operates at one speed and is intermittently run, data concerning the operating time of the pump over a given period can be used to generate the controlled amount difference. Those skilled in the art will appreciate that a variety of other pump control mechanisms can be utilized to provide data to an operating history module, which can be converted to a controlled amount difference.

Comparing a controlled amount difference (i.e., a measure of an amount of fluid based on control of pump operation) to a measured amount difference (e.g., based upon a change in reading in a level sensor of a reservoir) can provide an indication of whether an implantable infusion pump is operating in a nominal range. In one instance, the processor can be configured to trigger a leakage signal when the measured amount difference exceeds the valve amount difference by more than a designated leakage tolerance amount. In another instance, the processor can be configured to trigger a blockage signal when the valve amount difference exceeds the measured amount difference by a value greater than a blockage tolerance amount. Both the leakage tolerance amount and the blockage tolerance amount can be determined on the basis of pump characteristics, such as the typical amount of air bubbles in the fluid reservoir, and/or an acceptable minimum leakage for the infusion pump. The tolerance amounts can also be based in part on the characteristics of a sensor used to determine fluid amounts (e.g., the accuracy of the sensor).

In general, the processor can be configured in a variety of manners to actuate pump features on the basis of the comparison between a controlled amount difference and a measured amount difference, or some other comparison of one or more pump operational variables. For example, the processor can be configured to halt pump operation when a pump operational variable is detected to be outside a desired operating range, such as when the implantable infusion pump detects a temperature above 42° C. or below 36° C., corresponding with an anomalous patient temperature. In another example, the processor can be configured to sound an alarm, and/or halt operation, when the amount of fluid in the reservoir falls below a designated value. Other processor configurations can be developed to carry out the functions discussed with respect to the various methods described in the present application.

The exemplary embodiment of FIG. 4 presents one particular arrangement of components for a control system that can be used to manipulate measurement data associated with the reservoir of an implantable infusion pump. Those skilled in the art will readily appreciate that various hardware modifications can be made to the control system. For example, the valve history module 410 and measurement history module 420 are depicted as separate memory elements. Such memory element can span the range of types known to those skilled in the art. However, the history modules 410, 420 can be integrated together in a single memory device, or could be integrated as part of a larger memory device for the control system, or be integrated with the processor 430 as one microprocessor unit. As well, the real time clock can be part of the processor 430, or a separate unit as depicted in FIG. 4. Also, the processor can be embodied as a single physical device or a plurality of microprocessors that are integrated to perform the functions discussed with respect to the control system 400. Furthermore, as discussed relative to the valve history module, other types of operating history modules can also be implemented, without regard to the use of a valve. All these variations, among others, are within the scope of the present application.

Methods for Monitoring the Fluid in an Implantable Infusion Pump

Figure 5:
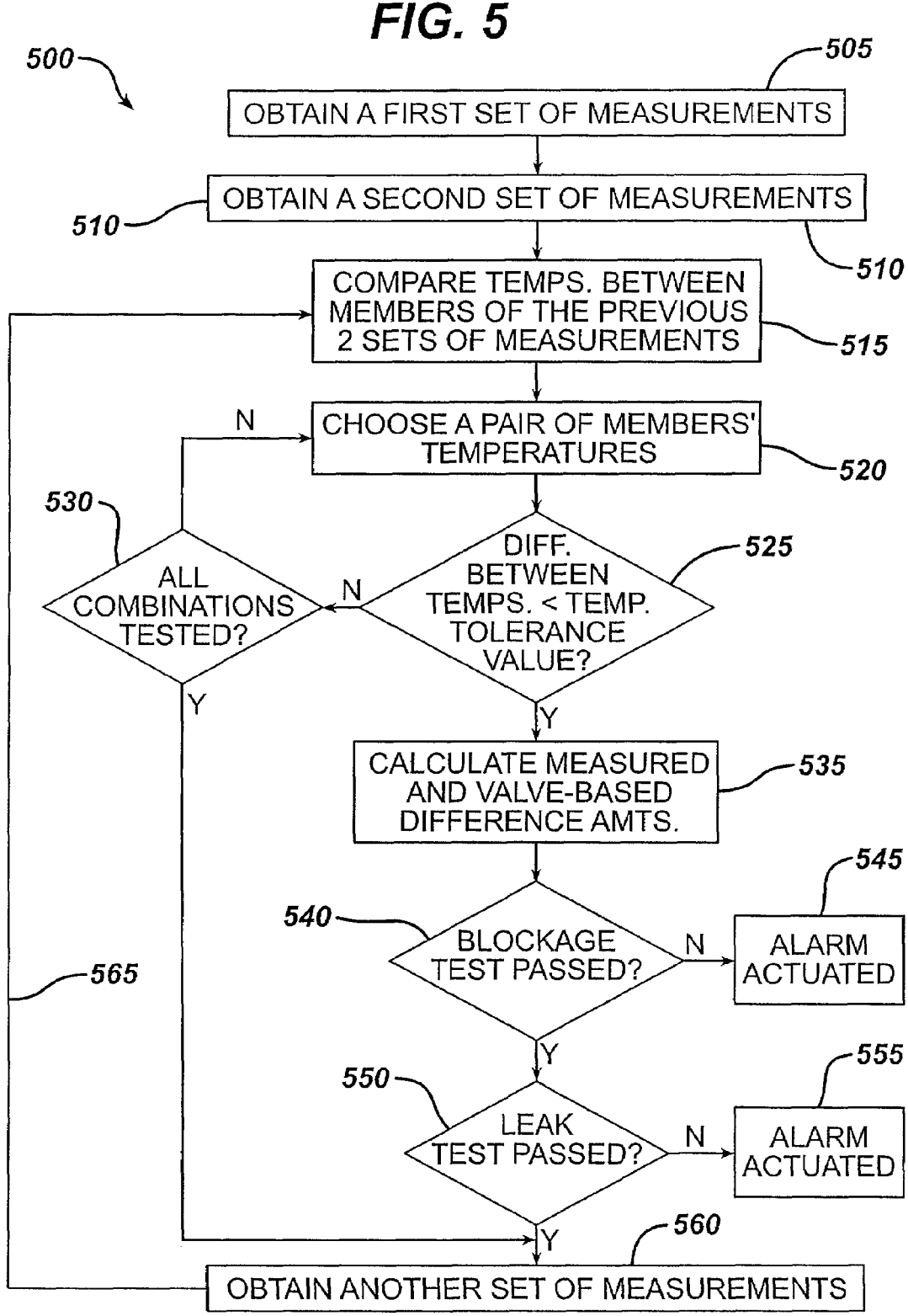
FIG. 5 presents a flow diagram of an exemplary method for monitoring fluid of an implantable infusion pump.

An exemplary embodiment of a method for monitoring fluid associated with an implantable infusion pump 500 is illustrated by the flow diagram shown in FIG. 5. A first set of measurements is obtained 505 from the reservoir of the implantable infusion pump, followed by a second set 510. Each set can contain one or more measurements, with each measurement including data regarding a fluid amount and temperature of fluid in the reservoir of the pump around some corresponding moment in time. The measurement can also include a time associated with obtaining the fluid amount and temperature data. In one instance, each set contains a plurality of measurements that are temporally spaced in a predetermined scheduled manner. The predetermined scheduled manner can be chosen such that a minimum desired amount of time has elapsed between the measurements in the first and second sets. For example, each set can include five measurements taken daily: one measurement is taken at a designated time each day, with measurements taken two hours and four hours before the designated time and two hours and four hours after the designated time. In another example, an earlier set includes five measurements as previously described. A later set is subsequently obtained having one measurement taken at the designated time, and two other measurements taken at two hours and four hours before the designated time. Other schedules can also be implemented.

The act of obtaining measurements can be integrated with other diagnostic tests for the implantable infusion pump. For example, with reference to utilizing the daily five measurement routine described above, the "designated time" can also correspond to a time each day where the implantable infusion pump performs one or more diagnostic tests to check the operability of various pump systems. Diagnostic tests can include computer memory checks, flash checks, battery voltage checks, temperature sensor checks, and fluid amount sensor checks. Clearly, other diagnostic tests can also be implemented as part of a global system for monitoring pump operability.

After the sets of measurements are obtained, a pair of measurements is identified for comparison 515. When an implantable infusion pump has temperature sensitive components, a comparison between two measurements can require a check that the temperatures of the measurements are within a designated operating range (e.g., an inductive coil as described herein). Accordingly, one measurement from each set can be chosen 520, and the corresponding difference between the temperatures can be compared relative to a temperature tolerance value 525. If the difference in temperatures is greater than the temperature tolerance value, then another pair of measurements is chosen for temperature comparison relative to the temperature tolerance value 520, 525; each pair of measurements can include one measurement from each of two sets. Optionally, each individual temperature can also be compared with a designated temperature range—if a measurement's corresponding temperature falls outside of the designated range, another pair of measurements is chosen. For example, when a measurement's corresponding temperature is above 42° C. or below 36° C., the measurement can be considered to fall outside the designated range.

Pairs of temperatures are continuously selected until a pair is found that has a temperature difference that is less than the temperature tolerance value. The order of selecting particular pairs of measurements for temperature difference comparison can depend upon the data associated with the measurements in the sets. In one instance, pairs of measurements can be selected on the basis of the time associated with a measurement (e.g., measurement pairs are chosen in the order of maximum time difference between the measurements). If all possible combinations of measurements between the two sets have been tested and none have a temperature difference less than the temperature tolerance value, the testing steps regarding the amount of fluid 535, 540, 550 are skipped until a new set of measurements is obtained 560, typically in accord with a predetermined scheduled manner as discussed earlier.

When the temperature difference between a pair of measurements is less than the temperature tolerance value, a measured amount difference can be calculated 535. The measured amount difference can be based at least in part upon fluid amounts corresponding with the first and second measurements. For example, the measured amount difference can be based upon two different amounts of fluid in a pump reservoir that are measured at two different instances in time. Such amounts can be determined by a measurement from a level sensor. Optionally, a controlled amount difference can also be identified. Such a controlled amount difference can be calculated on the basis of some controlled pump function such as the operating history of the valve over the time period between the identified pair of measurements. For example, the controlled amount difference can be calculated by the product of the total amount of time that a valve is placed in a particular open position during the period between the two measurements and the flow rate through the valve when the valve is in an open position.

If a measured amount difference and a controlled amount difference are calculated, the amount differences can be compared to evaluate the operation of the pump. In one particular instance, a comparison between the measured amount difference and the controlled amount difference can be performed to determine whether a blockage 540 has occurred in the pump. A blockage in the pump can cause less fluid to flow from the pump reservoir than expected when a valve is opened. For example, if the controlled amount difference exceeds the measured amount difference by more than a blockage tolerance value, an alarm can be actuated 545 to indicate that a blockage has occurred in the pump. In another instance, a comparison of the amount differences can be performed to determine whether a leak 550 is present in the pump. Leakages can be identified in circumstances in which more fluid drains from the pump reservoir than expected from the amount of time that a valve is opened. Thus, if the measured amount difference exceeds the controlled amount difference by more than a leakage tolerance amount, an alarm can be actuated 555 to indicate a leak in the pump system. Those skilled in the art will appreciate that other comparisons can also be utilized as a validation of pump operability. For example, if the controlled amount difference exceeds the measured amount difference by less than a blockage tolerance value and/or the measured amount difference exceeds the controlled amount difference by more than a leakage tolerance amount, a validation signal can be sent as an indicator that the tested operating parameters indicate pump operation within an expected range.

Comparison of a measured amount difference and a controlled amount difference can be predicated upon insuring that the infusion pump is operating within a specific range such that the comparison is valid. For example, if the controlled amount difference (e.g., the amount of fluid displaced from a reservoir based upon the valve operating history) over a period of time is less than volume of fluid corresponding with an error in the mechanism of the reservoir fluid amount sensor, a valid comparison cannot be performed. In another example, if the controlled amount difference over a period of time is greater than the maximum amount of fluid that can exit the reservoir over that period of time minus the volume of fluid corresponding with the reservoir sensor accuracy, again a valid comparison cannot be performed.

Those skilled in the art will appreciate that other comparisons can also be utilized as a validation of pump operability. For example, if the controlled amount difference exceeds the measured amount difference by less than a blockage tolerance value and/or the measured amount difference exceeds the controlled amount difference by more than a leakage tolerance amount, a validation signal can be sent as an indicator that the tested operating parameters indicate pump operation within an expected range Upon completion of comparisons between measured amount differences and valve amount differences 540, 550, another set of measurements can be obtained 560 in accord with the predetermined scheduled manner (e.g., performing five measurements in 2 hour intervals centered around a designed time). Subsequently, the steps of the method 500 can be repeated again 565 by comparing pairs of measurement temperatures such as utilizing one measurement from each of the last two sets of measurements taken 515, and following through with the remaining steps as diagrammed in FIG. 5. Thus, in an exemplary embodiment, a new set of measurements can be taken according to a predetermined scheduled manner (e.g., measurements taken every day), with the steps of choosing a pair of measurements 520, 525 and calculating a measured amount difference and a controlled amount difference based upon the selected measurements 535 being repeated. This process can be repeated throughout the operation of the pump to help insure desired operability of the pump.

Embodiments consistent with the methods described herein can be implemented with a variety of hardware and software configurations. For example, the control system depicted, and previously described, in FIG. 4 can be configured to carry out such methods. Those skilled in the art will appreciate that various elements of the control system (e.g., the processor, history modules, sensor, actuators, etc.) can be configured to carry out any number of the steps in the methods described herein. Furthermore, the skilled artisan recognizes that other equipment and electronic communication devices can also be configured to carry out the methods of the present application (e.g., a pump operating history module can be used to store operating history data regarding a pump's operating history to derive a controlled amount difference associated with a fluid reservoir). Though some embodiments are specifically described in the context of an implantable infusion pump, the methods and systems described can be effectively applied to other pumps (e.g., a peristaltic pump) or other fluid reservoir systems.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present invention. As well, one skilled in the art will appreciate further features and advantages of the invention based on the above-described embodiments. Accordingly, the invention is not to be limited by what has been particularly shown and described, except as indicated by the appended claims.

What is claimed is:

1. A method of monitoring fluid in a reservoir of an implantable infusion pump, comprising:
   a) obtaining a plurality of measurements from the reservoir, each measurement including corresponding data related to a fluid amount and a temperature;
   b) selecting a first measurement and a second measurement from the plurality of measurements such that a temperature difference based at least in part on temperatures corresponding with the first and second measurements is less than a temperature tolerance value; and
   c) calculating a measured amount difference based at least in part on fluid amounts corresponding with the first and second measurements.

2. The method of claim 1, wherein the step of obtaining the plurality of measurements includes:
   obtaining a first plurality of measurements, and
   obtaining a second plurality of measurements after the first plurality, and further wherein the step of selecting the first and second measurements includes selecting the first measurement from the first plurality and the second measurement from the second plurality.

3. The method of claim 2, wherein the step of selecting the first and second measurements includes:
   selecting a first candidate measurement from the first plurality,
   selecting a second candidate measurement from the second plurality, and
   replacing at least one of the first candidate measurement and the second candidate measurement if a temperature difference based at least in part on temperatures corresponding with the first and second candidate measurements is greater than the temperature tolerance value.

4. The method of claim 3, wherein each measurement of the plurality of measurements includes corresponding data related to a time, and further wherein the steps of selecting and replacing candidate measurements depends at least in part on the time corresponding with at least one candidate measurement.

5. The method of claim 3, wherein the step of replacing is repeated until the temperature difference is less than the temperature tolerance value.

6. The method of claim 1, further comprising:
   d) obtaining at least one additional measurement from the reservoir, each measurement including corresponding data related to the fluid amount and the temperature;
   e) selecting two measurements such that a temperature difference based at least in part on temperatures corresponding with the two measurements is less than the temperature tolerance value, at least one of the two measurements selected from the at least one additional measurement; and
   f) calculating a new measured amount difference based at least in part on the fluid amounts corresponding with the two measurements.

7. The method of claim 6, wherein steps d), e), and f) are repeated at least once during operation of the infusion pump.

8. A method of monitoring fluid flow from a reservoir of an implantable infusion pump, comprising:
   a) obtaining a plurality of measurements from the reservoir, each measurement including corresponding data related to a fluid amount, a temperature, and a time;
   b) selecting a first measurement and a second measurement from the plurality of measurements such that a temperature difference based at least in part on temperatures corresponding with the first and second measurements is less than a temperature tolerance value;
   c) calculating a measured amount difference based at least in part on fluid amounts corresponding with the first and second measurements.
   d) calculating a time difference based at least in part on times corresponding with the first and second measurements; and
   e) comparing the measured amount difference with a controlled amount difference, the controlled amount difference based at least in part on the time difference and operation of the implantable infusion pump to deliver fluid from the reservoir.

9. The method of claim 8, wherein the step of comparing the measured amount difference with the controlled amount difference is performed by comparing a measured flow rate with a controlled flow rate, the measured flow rate depending at least in part on the measured amount difference and the controlled flow rate depending at least in part on the controlled amount difference.

10. The method of claim 8, wherein the step of comparing includes determining a leakage in the implantable infusion pump when the measured amount difference exceeds the controlled amount difference by more than a leakage tolerance amount.

11. The method of claim 10, wherein the leakage tolerance amount is based at least in part on an accuracy of a level sensor used to identify an amount of fluid in the reservoir.

12. The method of claim 8, wherein the step of comparing includes determining a blockage in the implantable infusion pump when the controlled amount difference exceeds the measured amount difference by more than a blockage tolerance amount.

13. The method of claim 12, wherein the blockage tolerance amount is based at least in part on an accuracy of a level sensor used to identify an amount of fluid in the reservoir.

14. The method of claim 8, wherein the step of obtaining the plurality of measurements includes using a temperature-dependent level sensor to identify fluid amounts.

15. The method of claim 14, wherein the step of using the temperature dependent level sensor includes measuring an inductance of a coil coupled to the reservoir.

16. The method of claim 8, wherein the controlled amount difference is based at least in part on control electronics of the implantable infusion pump.

17. The method of claim 16, wherein the controlled amount difference is based at least in part on signals sent between the control electronics and a valve used to control flow from the reservoir.

18. The method of claim 16, wherein the step of obtaining the plurality of measurements includes sending a signal between the control electronics and a sensor to determine the fluid amount in the reservoir.

19. A control system for an implantable infusion pump, comprising:
   a measurement history module for storing a plurality of measurements, each measurement including corresponding data related to a temperature, a measured amount, and a time associated with measurements from the reservoir; and
   at least one processor electrically coupled to the measurement history module, the at least one processor configured to
   (i) select two measurements from the measurement history module such that a temperature difference based at least on temperatures corresponding with the two measurements is less than a temperature tolerance value, and
   (ii) calculate a measured amount difference based at least in part on measured amounts corresponding with the two measurements.

20. The control system of claim 19, wherein the measurement history module is in communication with a temperature-dependent level sensor for determining amounts of fluid in the reservoir.

21. The control system of claim 20, wherein the temperature-dependent level sensor includes an inductance-varying coil for determining the amounts of fluid in the reservoir.

22. The control system of claim 19, wherein the control system is embedded as a portion of the implantable infusion pump.

23. The control system of claim 19, further comprising:
   an operating history module for storing operating history data used to regulate flow from a reservoir of the infusion pump;
   wherein the at least one processor is electrically coupled to the operating history module, and further configured to
   (iii) calculate a time difference based at least in part on times corresponding with the two measurements,
   (iv) calculate a controlled amount difference based on the operating history and the time difference, and
   (v) compare the measured amount difference and the controlled amount difference.

24. The control system of claim 23, wherein the operating history module is a valve history module for storing operating history data of a valve.

25. The control system of claim 24, wherein the valve history module is configured to store operating history data that includes a total amount of time that the valve is disposed in at least one of an open position and a closed position over a selected period of time.

26. The control system of claim 23, wherein the at least one processor is configured to trigger a leakage signal when the measured amount difference exceeds the controlled amount difference by more than a leakage tolerance amount.

27. The control system of claim 23, wherein the at least one processor is configured to trigger a blockage signal when the controlled amount difference exceeds the measured amount difference by more than a blockage tolerance amount.

28. The control system of claim 23, wherein the at least one processor also calculates
   (vi) a measured flow rate based at least in part on the measured amount difference, and
   (vii) a controlled flow rate based at least in part on the controlled difference amount,
the at least one processor configured to compare the measured amount difference and the controlled amount difference by comparing the measured flow rate and the controlled flow rate.

29. The control system of claim 19, wherein the measurement history module and the at least one processor are each portions of a single microprocessor.

* * * * *